US012611551B2

(12) United States Patent
Wang

(10) Patent No.: US 12,611,551 B2
(45) Date of Patent: Apr. 28, 2026

(54) HEAD OPTICAL APPLICATION DEVICE, TRANSCRANIAL LIGHT REGULATION DEVICE AND NEAR INFRARED DEVICE

(71) Applicant: DANYANG HUICHUANG MEDICAL EQUIPMENT CO., LTD, Zhenjiang (CN)

(72) Inventor: Daifa Wang, Zhenjiang (CN)

(73) Assignee: DANYANG HUICHUANG MEDICAL EQUIPMENT CO., LTD, Zhenjiang (CN)

( * ) Notice: Subject to any disclaimer, the term of this patent is extended or adjusted under 35 U.S.C. 154(b) by 371 days.

(21) Appl. No.: 18/567,488

(22) PCT Filed: Jun. 21, 2021

(86) PCT No.: PCT/CN2021/101141
§ 371 (c)(1),
(2) Date: Dec. 6, 2023

(87) PCT Pub. No.: WO2022/257176
PCT Pub. Date: Nov. 15, 2022

(65) Prior Publication Data
US 2025/0121207 A1    Apr. 17, 2025

(30) Foreign Application Priority Data

Jun. 7, 2021    (CN) .......................... 202110631728.4

(51) Int. Cl.
*A61N 5/06* (2006.01)
(52) U.S. Cl.
CPC .... *A61N 5/0622* (2013.01); *A61N 2005/0651* (2013.01); *A61N 2005/0659* (2013.01)
(58) Field of Classification Search
CPC .......... A61N 5/0622; A61N 2005/0651; A61N 2005/0659; A61N 2005/0647;
(Continued)

(56) References Cited

U.S. PATENT DOCUMENTS

| | | | |
|---|---|---|---|
| 6,161,030 A | 12/2000 | Levendowski | |
| 6,201,982 B1 | 3/2001 | Menkes | |

(Continued)

FOREIGN PATENT DOCUMENTS

| | | | |
|---|---|---|---|
| CN | 103919547 A | 7/2014 | |
| CN | 106137135 A | 11/2016 | |

(Continued)

OTHER PUBLICATIONS

International Search Report issued in corresponding International Application No. PCT/CN2021/101141, dated Mar. 9, 2022, pp. 1-3, English Translation.

*Primary Examiner* — Jonathan T Kuo
(74) *Attorney, Agent, or Firm* — Carter, DeLuca & Farrell LLP

(57) ABSTRACT

The present disclosure provides a head optical application device, a transcranial light regulation apparatus and a near-infrared apparatus. The head optical application device comprises a support component, an optical component, and deployable components. The support component is constructed to mount an optical component. The optical component is constructed to transmit light to or receive light from scalp. The deployable components are provided on the support component, and are constructed to deploy or gather the distal ends under the action of force caused by the surrounding environment. Without the need for providing an electrical driving apparatus, the distal ends of the deployable components can be inserted into the user's hair gap in a gathered state, and distal ends of the deployable components can part (push) the hair blocking light (aside) in a deployed state after insertion, improving the problem of low light propagation rate due to hair blocking.

20 Claims, 11 Drawing Sheets

(58) Field of Classification Search
     CPC . A61N 5/06–2005/073; A61B 5/14553; A61B
                    5/0075; A61B 5/0082; A61B 5/14542;
                                           A61B 5/6803
     See application file for complete search history.

(56)                  References Cited

U.S. PATENT DOCUMENTS

| | | | |
|---|---|---|---|
| 7,201,764 B2 * | 4/2007 | Pearl | A61N 5/0617 128/898 |
| 8,285,355 B2 * | 10/2012 | Chen | A61B 5/291 600/383 |
| 12,114,996 B2 * | 10/2024 | Kumpan-Bahrami | G16H 20/30 |
| 2003/0093915 A1 * | 5/2003 | Pearl | A61N 5/0617 34/96 |
| 2011/0152659 A1 * | 6/2011 | Chen | A61B 5/291 600/372 |
| 2020/0221994 A1 * | 7/2020 | Kumpan-Bahrami | A61B 5/6803 |
| 2020/0275872 A1 | 9/2020 | Konoshita | |

FOREIGN PATENT DOCUMENTS

| | | |
|---|---|---|
| CN | 106510631 A | 3/2017 |
| CN | 106725308 A | 5/2017 |
| CN | 209404751 U | 9/2019 |
| WO | 2015/033440 A1 | 3/2015 |

* cited by examiner

HEAD OPTICAL APPLICATION DEVICE, TRANSCRANIAL LIGHT REGULATION DEVICE AND NEAR INFRARED DEVICE

CROSS REFERENCE TO RELATED APPLICATIONS

The present application is a national stage application of International Application No. PCT/CN2021/101141, filed Jun. 21, 2021, which claims the benefit of and priority to Chinese Patent Application No. 202110631728.4, filed Jun. 7, 2021, the entire contents of each of which are hereby incorporated by reference herein in their entirety.

TECHNICAL FIELD

The present disclosure relates to a technical field of medical equipment, especially relates to a head optical application device, a transcranial light regulation apparatus, and a near-infrared apparatus.

BACKGROUND

In recent years, scientific research has found that light can be applied in medicine, such as using light regulation to improve cerebral function for the research and treatment of neurological and mental diseases, or using light to measure brain blood oxygen signals for disease diagnosis and cerebral function analysis. During the use of existing transcranial light regulation products, the light emitted by the irradiation device is affected by the blocking of the user's hair, resulting in a decrease in the propagation rate of light, which makes most of the light unable to reach the user's scalp, and affects the effectiveness of transcranial light regulation products.

In addition, when using near-infrared spectroscopy technology to measure brain blood oxygen signals, the transmitting and receiving probes of near-infrared spectroscopy cerebral function imaging equipment are also affected by the user's hair blocking, making it difficult to obtain accurate and effective measurement results.

SUMMARY

In response to the aforementioned technical issues in existing technologies, the present disclosure provides a head optical application device, a transcranial light regulation apparatus, and a near-infrared apparatus, which can push the hair of users blocking light aside by means of deployable components to improve the propagation rate of light without depending on electric driving devices.

According to the first aspect of the present disclosure, a head optical application device is provided, which includes a support component, an optical component, and deployable components. The support component is constructed to mount the optical component. The optical component is constructed to transmit light to or receive light from scalp. The deployable components are arranged on the support component. Wherein, the deployable components are constructed to deploy or gather the distal ends thereof under the action of force caused by the surrounding environment.

According to the second aspect of the present disclosure, a transcranial light regulation apparatus is further provided, including a plurality of the head optical application devices as mentioned above and a housing for mounting the plurality of head optical application devices.

According to the third aspect of the present disclosure, a transcranial light regulation apparatus is further provided, including a plurality of the head optical application devices as mentioned above and an elastic cross-linked mesh for mounting the plurality of head optical application devices.

According to the fourth aspect of the present disclosure, a transcranial light regulation apparatus is further provided, including a plurality of the head optical application devices, as well as an elastic cross-linked mesh, and a housing for mounting the elastic cross-linked mesh. The plurality of head optical application devices are arranged on the elastic cross-linked mesh.

According to the fifth aspect of the present disclosure, a near-infrared apparatus is further provided, including a plurality of head optical application devices as mentioned above.

Compared with the prior art, the beneficial effect of the embodiments of the present disclosure is that the present disclosure enables the deployable components to gather or deploy with respect to each other on the distal side of the optical component under the action of force caused by the surrounding environment. Without the need for providing an electrical driving apparatus, the distal ends of the deployable components can be inserted into the user's hair gap in a gathered state, and distal ends of the deployable components can part (push) the hair blocking light (aside) in a deployed state after insertion, improving the problem of low light propagation rate due to hair blocking. Moreover, the use effect of the transcranial light regulation apparatus using the head optical application device can be improved, so that the light emitted by the optical component of the optical application device can directly irradiate the user's scalp and penetrate the skull, thereby better improving cerebral function. Similarly, the above structure can also improve the measurement effect of the near-infrared apparatus using the head optical application device, and achieve accurate and effective measurement results by parting the hair between the emitting probe and the receiving probe and the scalp.

BRIEF DESCRIPTION OF THE DRAWINGS

In figures that are not necessarily drawn to scale, the same reference numerals may describe similar components in different figures. The same reference signs with suffixes or different suffixes may denote different examples of similar components. The figures generally show various embodiments by way of example rather than limitation, and are used together with the description and the claims to describe the embodiments of the present disclosure. As proper, the same reference sign may be used throughout the drawings to denote the same or similar part. Such embodiments are illustrative, and are not intended to be exhaustive or exclusive embodiments of the present device or method.

Figure 1:
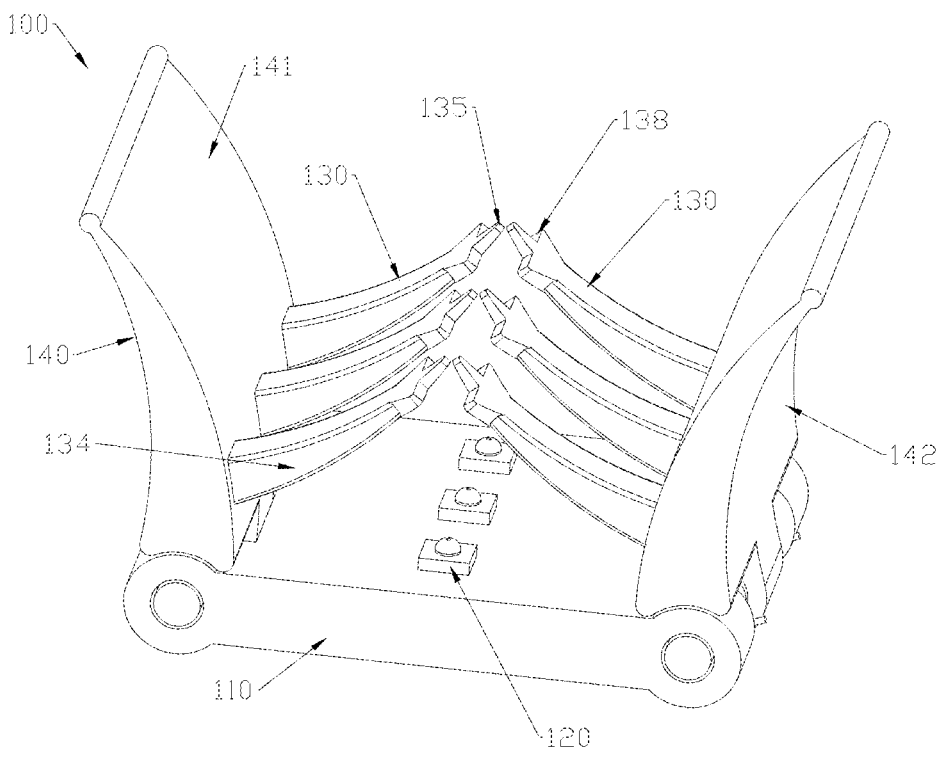
FIG. 1 is a first structural schematic diagram of the head optical application device according to the embodiment of the present disclosure, in which the deployable components are in a gathered state.

The components indicated by the reference signs in the figures are as follows:

100—head optical application device; 110—support component; 111—mounting plate; 112—first frame; 113—second frame; 114—first rotating portion; 115—limiting portion; 116—limiting groove; 117—third frame; 118—second rotating portion; 120—optical component; 130—deployable component; 131—arc-shaped convex portion; 132 insertion portion; 133—sliding guide surface; 134—deployment body; 135—arc-shaped portion; 136—first body; 137—second body; 138—stepped portion; 140—transmission mechanism; 141—first transmission portion; 142—second transmission portion; 143—sliding groove; 144—third transmission portion; 145—fourth transmission portion; 146—telescopic rod; 151—sleeve; 152—buffer spring; 153—spherical portion; 160—torsion component; 171—first bracket; 172—second bracket; 173—third bracket; 174—fourth bracket; 175—first substrate; 176—second substrate; 200—transcranial light regulation apparatus; 210—housing; 220—elastic cross-linked mesh; 300—headgear; 310—headgear body; 320—emitting probe; 330—receiving probe.

DETAILED DESCRIPTION

In order to enable those skilled in the art to better understand the technical solutions of the present disclosure, the present disclosure will be described in detail below in conjunction with the accompanying drawings and detailed embodiments. Embodiments of the present disclosure will be described in further detail below in conjunction with the accompanying drawings and detailed embodiments, but this is not intended to limit the present disclosure.

"First", "second" and similar words used in the present disclosure do not indicate any sequence, quantity or importance, but are only used for distincting different parts. Words like "including" or "comprising" mean that the elements preceding the word cover the elements listed after the word, and do not exclude the possibility of also covering other elements. The terms "up", "down", "left", "right", etc. are only used to represent relative positional relationships. When the absolute position of the described object changes, the relative positional relationship may also change accordingly.

In the present disclosure, when describing a specific device located between a first device and a second device, there may or may not be an intermediate device between the specific device and the first or second device. When describing the connection of a specific device to other devices, the specific device can be connected directly to the other devices without an intermediate device, or it can be connected indirectly to the other devices with an intermediate device.

All terms used in the present disclosure (including technical terms or scientific terms) have the same meanings as those understood by those skilled in the art to which the present disclosure belongs. It should also be understood that terms defined in general dictionaries should be interpreted as having meanings that are consistent with their meanings in the context of the relevant technology, and should not be interpreted in idealized or overly formal terms, unless explicitly defined here.

The techniques, methods, and equipments known to those skilled in the relevant art may not be discussed in detail, but in appropriate cases, the said techniques, methods, and equipments should be considered as a part of the description.

According to some embodiments of the present disclosure, a head optical application device 100 is provided. As shown in FIGS. 1 to 13, the head optical application device 100 includes a support component 110, an optical component 120, and deployable components 130. The support component 110 is constructed to mount the optical component 120. The optical component 120 is constructed to transmit light to or receive light from the scalp. The deployable components 130 are provided on the support component 110, wherein the deployable components 130 are constructed to deploy or gather the distal ends of the deployable components 130 under the action of force caused by the surrounding environment.

It should be noted that the apparatus mounted with the above head optical application device 100 can be worn on the user's head by the operator, and the above optical component 120 corresponds to the user's scalp. The wording "an optical component 120" does not intend to limit the number of the optical component 120 as 1, instead, it may cover one or more optical components 120. The proximal side referred to in the present disclosure is the side close to the operator and away from the user's scalp, the distal side is the side close to the user's scalp, the proximal end is the end far from the user's scalp, and the distal end is the end close to the user's scalp. The wording "proximal side" and "distal side" mentioned in the following text shall adopt this meaning.

Specifically, the above-mentioned head optical application device 100 includes but is not limited to being applied to transcranial light regulation apparatus 200 or near-infrared apparatus. The optical component 120 has the function of emitting light to or receiving light emitted from the user's scalp. The light can be infrared light that can penetrate the skull, and the optical component 120 can be any optical component 120 that can emit light, such as an LED lamp, fiber optic, laser, etc. When the head optical application device 100 is applied to transcranial light regulation products, the optical component 120 is mainly used to emit light to the scalp to improve the user's cerebral function. When the head optical application device 100 is applied to the field of near-infrared cerebral functional imaging technology, both the optical component 120 that can emit light and the optical component 120 that can receive light can be used to measure the user's brain blood oxygen signal. Of course, the above-mentioned head optical application device 100 can also be applied to other devices, mainly for receiving light emitted from the scalp. The present disclosure does not specifically define the role of the optical component 120 or the adaptation relationship between a plurality of optical components 120. Optical components 120 with corresponding functions can be adopted according to the technical field applied by the head optical application device 100 to improve the irradiation rate of the user's scalp.

The present disclosure does not specifically define the number and specific structure of deployable components 130, as long as the deployable components 130 are able to push the hair between the optical component 120 and the user's scalp aside. Preferably, the above deployable components 130 can be provided around the optical component 120 or in pairs on opposite sides of the optical component 120, so as to achieve a better effect of pushing hair aside, thus allowing the light emitted by the optical component 120 to directly illuminate the scalp, or receiving light from the scalp. The deployable component 130 can be any shape or structure that can achieve the hair pushing-aside effect, such as a comb shape, arc-shaped plate shape, triangular plate shape, or rectangular plate shape. The structures of the deployable components 130 in the drawings are only examples, and the present disclosure is not limited to this.

Specifically, the head optical application device 100 may include at least two deployable components 130, or only one deployable component 130. When the head optical application device 100 includes two deployable components 130, the distal end of each deployable component 130 can be deployed or gathered under action of the force caused by the surrounding environment, which is related to the relative position relationship between the deployable components 130. When the head optical application device 100 only includes one deployable component 130, the deployable component 130 can be composed of a plurality of claw shaped structures, and the plurality of claw shaped structures can be deployed and gathered. Based on specific embodiments, the number of deployable components 130 as mentioned above can be set based on structural selection. The following text uses at least two deployable components 130 as examples for explanation, but the present disclosure is not limited to this.

Specifically, among the deployable components 130, there is a gathered state where the distal ends gather with respect to each other, and also a deployed state where the distal ends deploy with respect to each other. When the apparatus mounted with the head optical application device 100 is worn on the user's head, the distal ends of the deployable components 130 are in a gathered state, and the sectional area of the distal ends of the deployable components 130 can be minimized as much as possible to facilitate insertion into the hair. After the user already wears the above equipment, the distal ends of the deployable components 130 maintain a snugly fitting relationship with the user's scalp, so that under action of the force caused by the surrounding environment, the distal ends of the deployable components 130 can be deployed from each other. When it is transformed into a deployed state, the deployable component 130 can push and bring the hair in the area illuminated by the optical component 120 aside in a direction of departing from that area, so as to achieve the goal of pushing aside the hair and thus increasing the transmission rate of light.

In some embodiments, the force caused by the surrounding environment can be understood as the force caused by changes in temperature, humidity, and other factors in the surrounding environment, or the force manually applied by the surrounding operator. It should be emphasized that the force caused by the surrounding environment are not caused by the driving of electric driving equipment. Although electric drive can achieve the control of the deploying or gathering of the deployable component 130, the solution based on drive needs to provide a power source. It has complex structure and high cost issue. Among them, electric driving equipment can be understood as pneumatic mechanisms, electromagnetic control mechanisms, or other devices that can be powered by a power supply for operation. The temperature, humidity, and other changes in the surrounding environment as mentioned above can lead to changes in the structure of the support component 110 and/or the deployable component 130.

Specifically, the above deployable component 130 can be connected to the support component 110 through rotational connection, detachable connection, or other components. The rotational connection may include but is not limited to pivotable connection, as long as the deployable component 130 can be deployed or gathered under the force caused by the surrounding environment.

Specifically, the support component 110 and/or the deployable component 130 may be made of materials whose structure can change with the change of temperature. When the temperature of the surrounding environment is within the first preset temperature range, the support surface of the support component 110 on which the deployable component 130 is provided can form a concave cavity towards the proximal side direction. When the user wears the head optical application device 100, the distal ends of the deployable components 130 abut against the user's scalp in a gathered state. When the temperature of the surrounding environment reaches a second preset temperature, the structure of the support component 110 changes due to the temperature of the surrounding environment. The support surface, on which the deployable components 130 are provided, gradually changes from inward concave from the proximal side to outward convex, so that deployable components 130 can gradually deploy outward and transform into a deployed state with the deformation of the support surface while abutting against the scalp, so as to achieve hair pushing-aside. The first preset temperature mentioned above can be room temperature (such as 18 degrees Celsius to 25 degrees Celsius), while the second preset temperature is a temperature higher than room temperature, which corresponds to the temperature at which deformation can occur in the material used in the support component 110 and/or the deployable component 130. The following will provide a specific explanation of embodiments where the structure of the deployable component 130 can vary with temperature, and will not be elaborated here.

In some embodiments, when the deployable components 130 are in a gathered state, each deployable component 130 can be provided in a conical shape, and the tip of the conical shape is arranged in relation to the optical path of the optical component 120 for emitting or receiving light, such as on the optical path. In this manner, when the deployable components 130 are transformed into a deployed state, the hair on the optical path of the optical component 120 is pushed aside to improve the light propagation rate along the optical path relative to the scalp.

Figure 2:
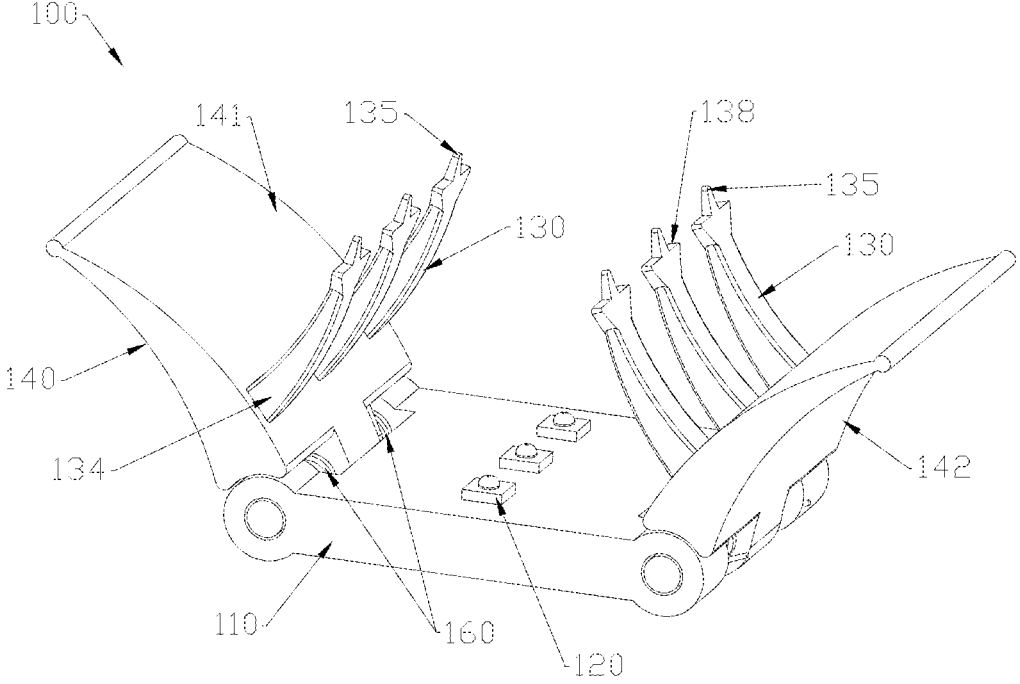
FIG. 2 is a first structural schematic diagram of the head optical application device according to the embodiment of the present disclosure, in which the deployable components are in a deployed state.
Figures 3, 4:
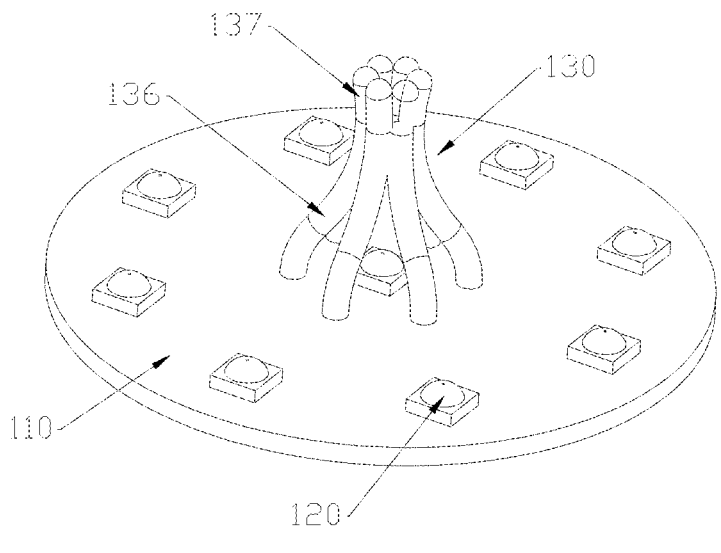
FIG. 3 is a second structural schematic diagram of the head optical application device according to the embodiment of the present disclosure, in which the deployable components are in a gathered state.
FIG. 4 is a third structural schematic diagram of the head optical application device according to the embodiment of the present disclosure, in which the deployable components are in a gathered state.

Specifically, the present disclosure does not specifically define on the shape and material of the above-mentioned support component 110, which can be in any arbitrary shape such as a circular plate shape, rectangular plate shape, or block shape, as long as it can carry the optical component 120 and the deployable component 130. The structural design of the above support component 110 should minimize its occupied space as much as possible, and be made of materials with strong structural strength and light material weight, so as to maintain stable mounting while reducing the pressure on the user's head when wearing, and improving the user's experience. Specifically, as shown in FIGS. 1 to 4, the support components 110 shown in FIGS. 1 to 2 are both rectangular plate shape, while the support components 110 shown in FIGS. 3 to 4 are both circular plate shape. It can be understood that the structure of the support component 110 can be selectively designed based on the specific structure of the head optical application device 100, and the present disclosure does not specifically limit this.

The present disclosure enables the deployable components 130 to gather or deploy with respect to each other on the distal side of the optical component 120 under the action of force caused by the surrounding environment. Without the need for providing an electrical driving apparatus, the distal ends of the deployable components 130 can be inserted into the user's hair gap in a gathered state, and distal ends of the deployable components 130 can push the hair blocking light aside in a deployed state after insertion, improving the problem of low light propagation rate caused by hair blocking.

Moreover, the use effect of the transcranial light regulation apparatus 200 using the head optical application device 100 can be improved, so that the light emitted by the optical component 120 of the optical application device can irradiate directly the user's scalp and penetrate the skull, thereby better improving cerebral function. Similarly, the above structure can also improve the measurement effect of the near-infrared apparatus using the head optical application device 100, and achieve accurate and effective measurement results by pushing the hair between the emitting probe 320 and the receiving probe 330 and the scalp aside.

In some embodiments, the deployable component 130 is made of a first deformable material and undergoes a transformation between the first configuration that the deployable components 130 gather at the distal end and the second configuration that the deployable components 130 deploy at the distal end under action of the deformation stress of the first deformable material caused by the surrounding environment.

Specifically, the first deformable material as mentioned above can be a memory material, such as shape memory polymers, shape memory metals (such as nickel titanium shape memory alloys), etc. The memory material can be molded into one configuration under the environment of the second preset temperature, transformed to another configuration under the environment of the first preset temperature, and transformed to the previous configuration immediately upon the surrounding environment returns to the second preset temperature.

The following is an example of the deployable component 130 using memory materials. For example, the deployable component 130 is made of shape memory alloy with two-way memory effect, and deployable components 130 can be in a gathered state at low temperature. The above first configuration of the deployable components 130 can be understood as being associated with this gathered state. After the surrounding environmental temperature rises to the temperature at which the shape memory alloy can deform, the deployable components 130 undergo deformation and transform into a deployed state due to its own material, The second configuration can be understood as being associated with the deployed state.

In some embodiments, in the case where the first deformable material used in each deployable component 130 undergoes deformation under the influence of temperature, the change of temperature in the surrounding environment can be provided by a heating element, or by the heat generated after the operation of the optical component 120, or by other devices on the apparatus using the head optical application device 100 that can increase the surrounding environment temperature. The present disclosure does not specifically limit this. Preferably, the temperature of the surrounding environment is provided by the heat generated after the operation of the optical component 120, so as to utilize the temperature increase effect generated by the operation of the optical component 120 to make each deployable component 130 to undergo deformation after the operation of the optical component 120, transforming from the first configuration to the second configuration. After the end of use of the optical component 120, the temperature of the surrounding environment gradually decreases, causing the deployable components 130 to gradually transform from the second configuration to the first configuration. There is no need to use other heating elements to provide heat, and no additional operation of the operator is required to transform the deployable component 130 between the two configurations, which not only reduces costs but also facilitates the operator's use.

In some embodiments, the first deformable material as mentioned above can be a shape memory material, which can be a linear polymer containing partial crystalline polymerized from three kinds of monomeric raw materials: isocyanate, polyol, and chain extender. It can form reversible transformation between the glassy state and the rubbery state, and can be restored to its original shape when heated to 40 degrees Celsius. The deployable component 130 can be transformed between the two configurations without other means, making the structure of the deployable component 130 simpler and lower in cost.

In some embodiments, the first deformable material as mentioned above can be a photoinduced shape memory polymer, which contains photochromic genes. The light emitted by the optical component 120 can be used to transform the deployable component 130 from the first configuration to the second configuration. That is, the light emitted by the optical component 120 can be used not only for treatment or measurement, but also for making the distal ends of the deployable components 130 gather or deploy with respect to each other without adding other structural designs, thus making the structure of the head optical application device 100 simpler and the cost cheaper.

The deployable component 130 made of the shape memory polymer as mentioned above has a lighter weight and lower price compared to the deployable component 130 made of the memory alloy at the same size. Additionally, the deployable component 130 made of the shape memory polymer as mentioned above has a larger deformation variable and has the effect of repeatable deformation.

The above is an example of memory materials that can undergo deformation under the influence of temperature and irradiation, but the present disclosure is not limited to this. The above-mentioned memory material can be a material that can transform the deployable component 130 between the two configurations using one or more methods such as thermal, electrical, optical, magnetic, etc. The deployable component 130 can be made of at least one of the above memory materials. A device that satisfies the condition for memory material to undergo deformation or achieves this condition can be provided in the head optical application device 100 or the apparatus mounted with the head optical application device 100. The present disclosure does not specifically limit this, as long as it can enable the deployable components 130 to transform between the deployed state and the gathered state.

Moreover, the above deployable component 130 can be made entirely of a first deformable material or partially of the first deformable material. Preferably, when a portion of the deployable component 130 is made of the first deform-able material, the distal side of the above deployable component 130 can be made of the first deformable material. In addition, when the deployable component 130 is made of memory alloy, it can be wrapped with a layer of soft material outside to improve the comfort of the user when the deploy-able component 130 comes into contact with the scalp.

In some embodiments, the deployable components 130 are constructed to deploy or gather the distal ends of the deployable components 130 under the action of manual force in the surrounding environment.

Specifically, the above manual force in the surrounding environment can act on the support component 110, enabling it to move along a first direction towards the scalp and/or along a second direction away from the scalp, or move up and down in the direction of hair growth, or rotate relative to the user's scalp. The following will provide a detailed explanation of a plurality of specific embodiments in which the distal ends of the deployable components 130 are deployed or gathered with respect to each other through different movements of the support component 110.

In part of the following embodiments, the head optical application device 100 may further include a transmission mechanism 140 located between the support component 110 and the deployable component 130. The transmission mechanism 140 is constructed to transform the translational motion or rotational motion of the support component 110 into deploying and gathering of the distal ends of the deployable component 130. The translational motion or rotational motion of the above support component 110 can be transmitted through the transmission mechanism 140, enabling the deployable component 130 to transform between the deployed state and gathered state.

Specifically, the support component 110 is further con-structed to move along the first direction towards the distal side under the action of manual force; or it can rise and fall along the second direction of hair growth under the action of manual force. The above translational motion includes motion along the first direction and motion along the second direction.

Embodiment 1

As shown in FIGS. 1 to 5, the support component 110 shown in the drawings can deploy or gather the distal ends of the deployable components 130 with respect to each other under the action of manual force in the surrounding envi-ronment.

Combining FIGS. 1 and 2, when the apparatus mounted with the head optical application device 100 is worn on the user's head, the deployable component 130 in FIGS. 1 and 2 abuts against the user's scalp, and the operator can act on the support component 110 through manual force, causing the support component 110 to move along the first direction towards the scalp. In some embodiments, as shown in FIGS. 1 and 2, the transmission mechanism 140 includes a first transmission portion 141 and a second transmission portion 142 respectively pivotally connected to the opposite sides of the support component 110. The deployable components 130 are at least two, and are respectively located on the inner sides of the first transmission portion 141 and the second transmission portion 142. Each of the first transmission portion 141 and the second transmission portion 142 is constructed to expand outward as the support component 110 translates along the first direction, such that the deploy-able components 130 located thereon deploy from each other.

Specifically, as shown in FIGS. 1 and 2, the shapes of the first transmission portion 141 and the second transmission portion 142 can be in a relatively deployed state when the deployable components 130 are in a gathered state or deployed state, so that when the deployable components 130 are in a gathered state, the first transmission portion 141 and the second transmission portion 142 can move towards the first direction under the action of the support component 110, gradually deploy from the state shown in FIG. 1 to the deployed state shown in FIG. 2, so as to carry the distal ends of the deployable components 130 to depart from each other.

In some embodiments, as shown in FIGS. 1 and 2, both the above first transmission portion 141 and the second transmission portion 142 can be arc-shaped plates. The arc-shaped design of the arc-shaped plate should facilitate the gradual outward deploying of the two when subjected to a force in the first direction, and the arc-shaped plate structure increases the structural strength of the transmission mechanism 140, so that when the first transmission portion 141 and the second transmission portion 142 are subjected to force, they can smoothly carry and drive the distal ends of the deployable components 130 away from each other.

In some embodiments, a plurality of deployable compo-nents 130 located on the first transmission portion 141 can be integrally formed on the first transmission portion 141, and a plurality of deployable components 130 located on the second transmission portion 142 can be integrally formed on the second transmission portion 142, so as to facilitate maintaining the relative position relationship between the transmission component and the deployable component 130 and ensure the structural strength at the connection between the two.

In some embodiments, the deployable component 130 is made of a second deformable material, and the support component 110 is further constructed to enable the distal ends of the deployable component 130 to transform from gathering to deploying through deformation when moving along the first direction towards the distal side under the action of manual force.

Specifically, the second deformable material can be the same material as the first deformable material or a different material. When the two are different, the second deformable material can be a material that can undergo elastic deformation, either metallic material or non-metallic material, such as phosphorus bronze, beryllium bronze, manganese steel, etc. of metallic materials, or rubber, silicone, etc. of non-metallic materials. The present disclosure does not provide specific limitations on this matter. As long as the second deformable material can undergo deformation under force and return to the state before the force is applied when the force is withdrawn.

As shown in FIGS. 1 and 2, the number of deployable components 130 shown in FIG. 1 is six, and of course, a plurality of deployable components 130 can also be provided along the first direction. In the figures, three deployable components 130 are set on one side of the optical component 120 as an example for illustration, and the present disclosure is not limited to this. As shown in FIG. 1, the shapes of the deployment bodies 134 of the deployable components 130 located on the two opposite sides of the optical component 120 are constructed to expand outward from each other, so as to facilitate the trend movement of the deployable components 130 provided in pairs transforming into the deployed state.

Figure 5:
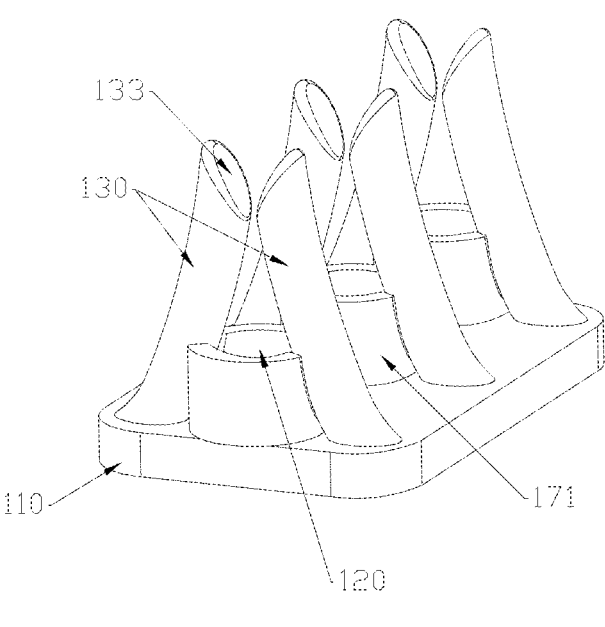
FIG. 5 is a fourth structural schematic diagram of the head optical application device according to the embodiment of the present disclosure, in which the deployable components are in a gathered state.

Specifically, in conjunction with FIGS. 3 to 5, the deployable components 130 in FIGS. 3 to 5 each can be made of a second deformable material. When the apparatus mounted with the head optical application device 100 is worn on the user's head, there is a certain gap between the distal ends of deployable components 130 and the user's scalp to avoid irregular deformation caused by the scalp acting on the deployable component 130 during wearing. After wearing the above apparatus, the operator can act on the support component 110 to move it along the first direction. At this time, the deployable components 130 are squeezed between the support component 110 and the scalp, and the deployable components 130 undergo elastic deformation and gradually transform into a deployed state to push the hair aside during the deployment process.

In some embodiments, as shown in FIG. 3, there are at least two deployable components 130, each of which includes a first body 136 provided on the support component 110 and a second body 137 provided on the distal side of the first body 136. The proximal ends of the second bodies 137 of the deployable components 130 lean against each other and gradually deploy towards their distal ends.

Specifically, the above second body 137 is formed by extending outward along the length direction of the first body 136, and the proximal ends of a plurality of second bodies 137 can gather with respect to each other under the action of magnetic components or elastic bands. The distal ends of a plurality of second bodies 137 are deployed with respect to their proximal ends, which facilitates the transformation of the second body 137 to the deployed state. In this way, the hair can be smoothly pushed aside to achieve better hair pushing-aside effect.

In some embodiments, the first body 136 and the second body 137 can be integrally formed, wrapped and molded, or the first body 136 and the second body 137 can be connected by adhesive bonding or other connection methods, which is not specifically limited in the present disclosure.

In some embodiments, the second body 137 is closer to the user's scalp with respect to the first body 136. The second body 137 can be made of materials with relatively higher flexibility to ensure the comfort degree when it is in contact with the user's scalp, and the first body 136 is made of materials with relatively higher hardness, which can further ensure that the deployable components 130 can be smoothly deployed with respect to each other during the deployment process without any inward or lateral bending that affects the hair pushing-aside effect.

In some embodiments, as shown in FIG. 5, a sliding guide surface 133 is provided on the distal end of the deployable component 130, and the sliding guide surface 133 is constructed so that the force applied to the distal end of the deployable component 130 for deploying is greater than the force applied to the distal end of the deployable component 130 for gathering, so that the deployable components 130 can be smoothly deployed when squeezed between the support component 110 and the scalp.

Specifically, the above-mentioned sliding guide surface 133 can be made of smooth material to reduce friction between the deployable components 130 and the scalp, facilitating the relative deployment and expansion of the deployable components 130.

Specifically, as shown in FIG. 5, the deployable components 130 are arranged in pairs on two opposite sides of the optical component 120, and a first bracket 171 is provided between the deployable components 130 arranged in pairs. The first bracket 171 corresponds to the optical component 120 one by one, and the first bracket 171 forms a connected cavity, and the optical component 120 can be embedded in the connected cavity. The first bracket 171 mentioned above is constructed to apply a push force to deployable components 130 to make them deploy outward when the deployable components 130 are subjected to force. The above structure can achieve a good hair pushing-aside effect, allowing more irradiations from the optical component 120 to reach the scalp, further improving the irradiation rate to the head.

In some embodiments, the optical component 120 may be one or more. When there are a plurality of optical components 120 (as shown in FIG. 4), the support component 110 is in a circular plate shape, and the optical components 120 are plural. One of the optical components 120 is located in the center of the support component 110, and the other optical components 120 are provided around the optical component 120 in the center, and a plurality of deployable components 130 are provided around the optical component 120 in the center. There is also a second support 172 provided around the optical component 120 on the support component 110. The second bracket 172 is constructed to apply a push force to deployable components 130 to make them deploy outward when deployable components 130 are subjected to force, in order to facilitate the parting and pushing-aside of the hair. In some embodiments, the deployable component 130 may be provided around a plurality of optical components 120.

Specifically, as shown in FIG. 2, a torsion component 160 that makes the distal ends of the deployable components 130 gather with respect to each other is provided at the pivot connection between the deployable component 130 and the support component 110. The torsion component 160 can be a torsion spring. After the use of the head optical application device 100 is finished, there is no need to manually reset the deployable components 130. Under the action of the torsion component 160, the distal ends of the deployable components 130 will be reset and transformed into a gathered state.

Embodiment 2

As shown in FIGS. 6 to 9, the support component 110 includes a mounting plate 111 for mounting the optical component 120, the deployable components 130 are at least two, each of which is pivotally connected to the mounting plate 111 and distributed on two opposite sides of the optical component 120. The transmission mechanism 140 includes a pair of sliding grooves 143 extending along direction of hair growth, a third transmission portion 144 and a fourth transmission portion 145 sliding along the sliding groove 143. The spacing between the paired sliding grooves 143 gradually narrows along the direction of hair growth, the respective end of the third transmission portion 144 and the fourth transmission portion 145 departing from the sliding groove 143 abuts against the proximal side of the deployable component 130.

Figure 6:
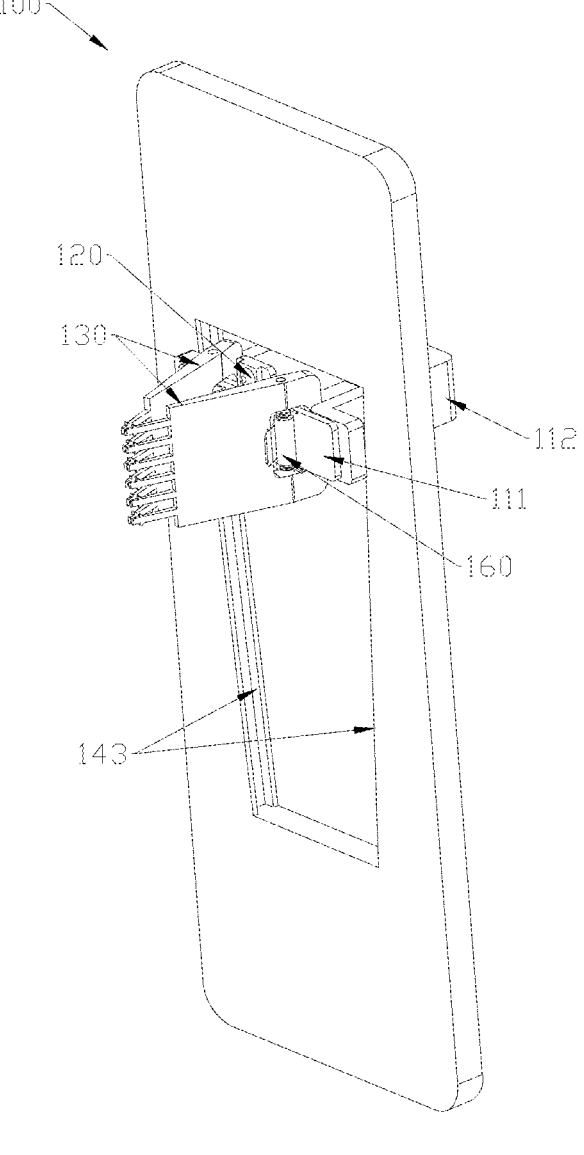
FIG. 6 is a fifth structural schematic diagram of the head optical application device according to the embodiment of the present disclosure, in which the deployable components are in a gathered state.
Figure 7:
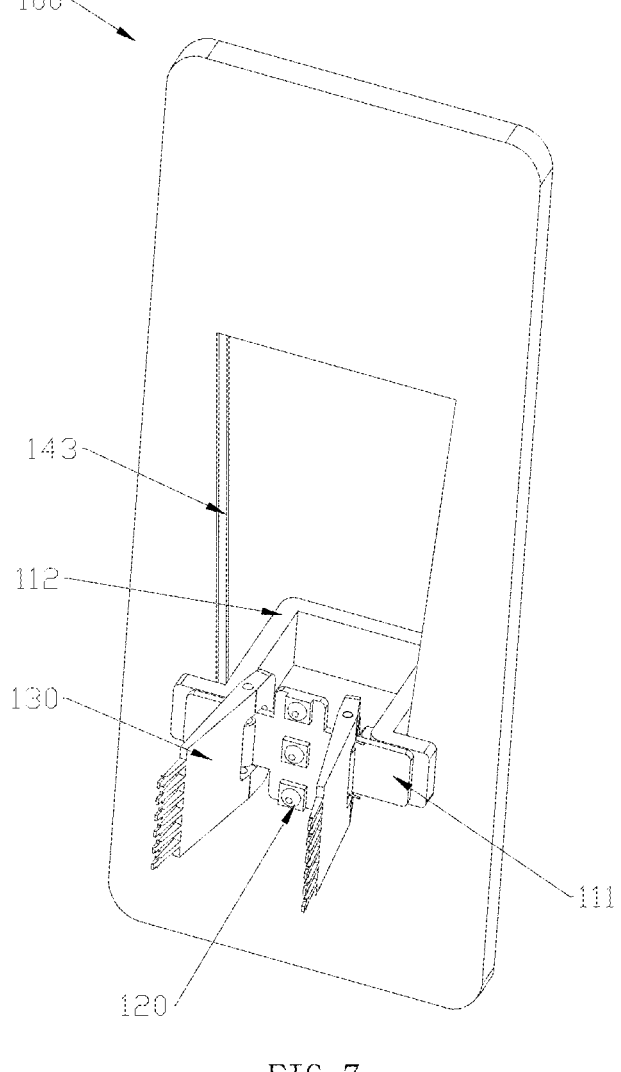
FIG. 7 is a fifth structural schematic diagram of the head optical application device according to the embodiment of the present disclosure, in which the deployable components are in a deployed state.

Specifically, FIGS. 6 and 7 illustrate the schematic diagram of the use state of the head optical application device 100 when the user's upper body is in an upright state. The direction from top to bottom shown in FIG. 6 is the direction of hair growth.

Specifically, the third transmission portion 144 and the fourth transmission portion 145 mentioned above can approach or depart from each other with the variation of the spacing between the paired sliding grooves 143. As shown in FIG. 6, the head optical application device 100 is in a state where no force is applied. At this time, the deployable components 130 are in a gathered state, and the spacing between the paired sliding grooves 143 is also relatively large. When a force is applied to the mounting plate 111, causing the mounting plate 111 and the deployable component 130 to move in the direction of hair growth (as shown in FIG. 7), the spacing between the paired sliding grooves 143 gradually decreases, causing the third transmission portion 144 and the fourth transmission portion 145 to move in a direction approaching each other. The two act on the proximal sides of the deployable component 130 respectively, causing the deployable component 130 to pivot to a configuration with the proximal side gathering with respect to each other while the distal side deploying with respect to each other, so as to part and push the hair aside in the corresponding area.

Specifically, the deployable component 130 can be any shape or structure that can achieve the hair pushing-aside effect, such as an arc-shaped plate, a comb shaped, a triangular plate, or a rectangular plate. The shape of the deployable component 130 shown in FIGS. 6 and 7 as a rectangular plate is only an example, and the present disclosure is not limited to this.

Figure 8:
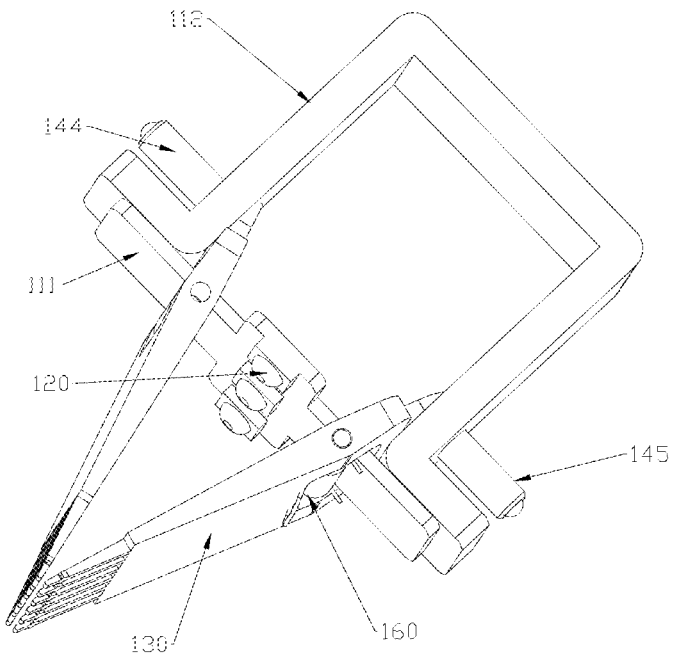
FIG. 8 is a partial structural schematic diagram of the fifth structure of the head optical application device according to the embodiment of the present disclosure.

Specifically, as shown in FIG. 8, a torsion component 160 is provided at the pivot connection between the deployable component 130 and the support component 110, the torsion component 160 makes the distal ends of the opposite deployable components 130 gather with respect to each other. The torsion component 160 can be a torsion spring. After the use of the head optical application device 100 ends, there is no need to manually reset each deployable component 130. Under the action of the torsion component 160, the deployable component 130 and the mounting plate 111 will be reset.

In some embodiments, the support component 110 further includes a first frame 112, a mounting plate 111 is provided on the distal side of the first frame 112, the proximal side of the first frame 112 is configured to receive manual force, and there are through holes on the two opposite sides of the first frame 112 that allow the third transmission portion 144 and the fourth transmission portion 145 to pass through.

Specifically, the proximal side of the first frame 112 can pass through the outer housing 210 of the apparatus mounted with the head optical application device 100. When the device is worn on the user's head, the operator can move the portion of the first frame 112 that is exposed outside the housing 210.

Specifically, the above first frame 112 can have a U-shaped body, which includes two opposite vertical plates and a horizontal plate connecting the two vertical plates. The above through holes are respectively provided on the two vertical plates, and the two through holes are oppositely provided. By providing the above-mentioned through holes, the positions of the third transmission portion 144 and the fourth transmission portion 145 can be radially limited, so that the third transmission portion 144 and the fourth transmission portion 145 can stably stretch and retract in their axial directions. The above horizontal plate is configured to receive manual force, which is beneficial for the operator to apply force.

Figure 9:
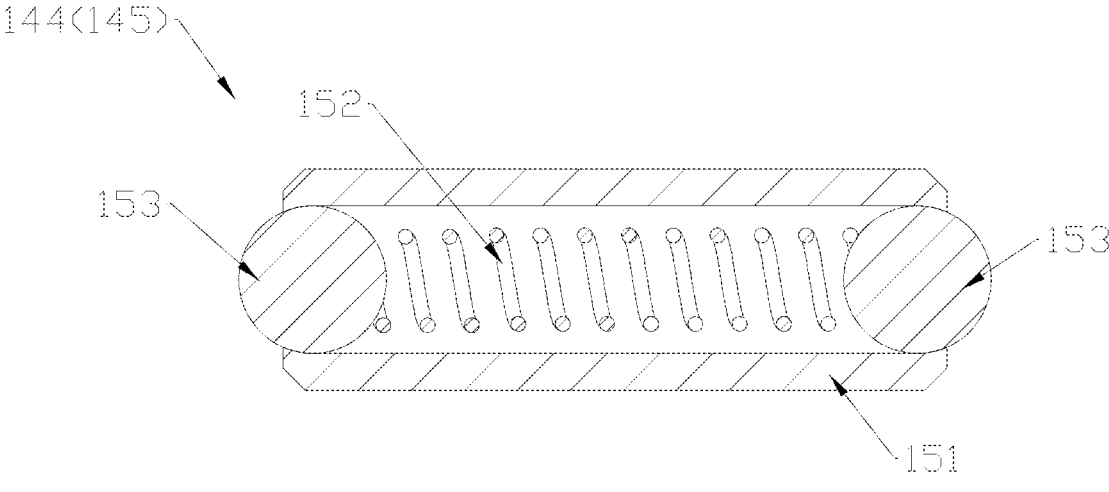
FIG. 9 is a sectional view of a third transmission portion or a fourth transmission portion of the head optical application device according to the embodiment of the present disclosure.

In some embodiments, as shown in FIGS. 8 and 9, FIG. 9 is a cross-sectional view of the third transmission portion 144 or the fourth transmission portion 145. Each of the third transmission portion 144 and the fourth transmission portion 145 includes a sleeve 151, a buffer spring 152 located inside the sleeve 151, and spherical portions 153 that respectively abut against both ends of the buffer spring 152. One of the two spherical portions 153 is embedded in the sliding groove 143, and the other abuts against the deployable component 130. A part of the above-mentioned spherical portions 153 can be embedded into the sliding groove 143, and the structural design of the spherical portion 153 can reduce the friction between it and the sliding groove 143, facilitating the sliding of the third transmission portion 144 and the fourth transmission portion 145 along the sliding groove 143.

Specifically, the above buffer spring 152 is used to apply force to the two spherical portions 153 that departs them with respect to each other. The two ports of the above-mentioned sleeve 151 can be constructed to block the spherical portions 153 from completely detaching from the sleeve 151.

Embodiment 3

Figure 10:
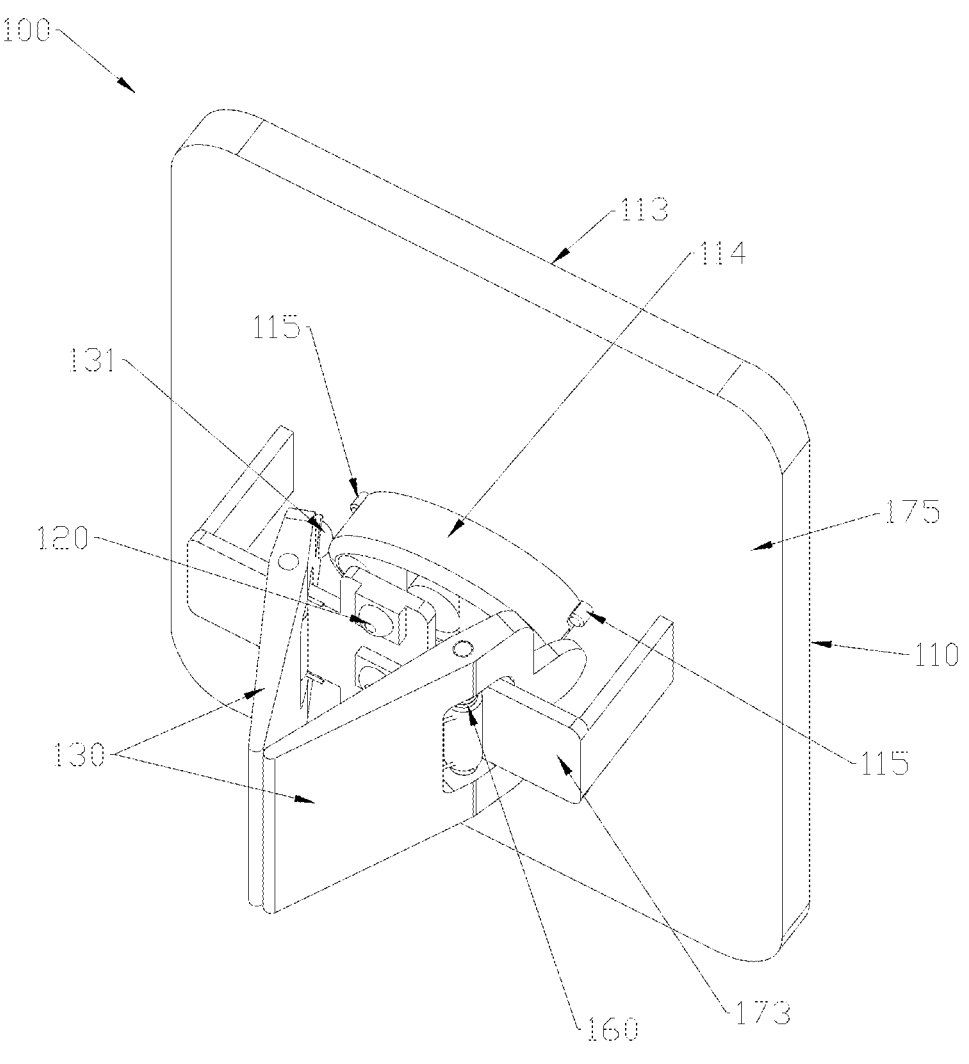
FIG. 10 is a sixth structural schematic diagram of the head optical application device according to the embodiment of the present disclosure, in which the deployable components are in a gathered state.
Figure 11:
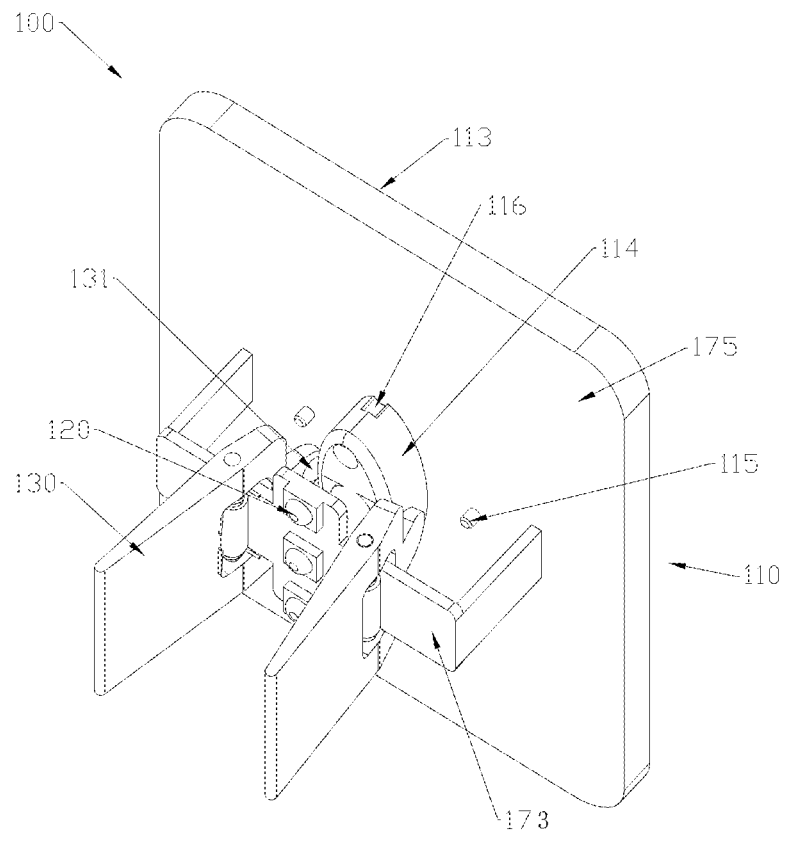
FIG. 11 is a sixth structural schematic diagram of the head optical application device according to the embodiment of the present disclosure, in which the deployable components are in a deployed state.

As shown in FIGS. 10 and 11, the support component 110 includes a second frame 113 and a first rotating portion 114 rotatably provided on the second frame 113. There are at least two deployable components 130, each of which is pivotally connected to the second frame 113 and distributed on the two opposite sides of the optical component 120. The surface of each deployable component 130 on the proximal inner side abuts against the circumferential outer wall of the first rotating portion 114. The first rotating portion 114 is constructed to drive, by means of rotation, the proximal ends of the deployable components 130 located on two opposite sides of the optical component 120 to deploy or gather with respect to each other.

Specifically, the above first rotating portion 114 may have two opposite sides spaced at a first length, and other two opposite sides spaced at a second length, wherein the first length is greater than the second length. When the two sides spaced at the first length respectively abut against the proximal sides of the oppositely provided deployable components 130, the deployable components 130 are in a gathered state (as shown in FIG. 10). When the operator rotates the first rotating portion 114 to make the two sides with a spacing of the second length abut respectively against the deployable components 130, the deployable components 130 gradually transform from the gathered state to the deployed state (as shown in FIG. 11).

Specifically, the cross-sectional shape of the first rotating portion 114 mentioned above can be elliptical shape, irregularly arc shape, rectangular shape, or other shapes, and the present disclosure does not specifically limit this. Preferably, as shown in FIG. 11, the cross-sectional shape of the first rotating portion 114 is elliptical, allowing the deployable components 130 to gradually deploy from a gathered state, improving the user's use experience.

In some embodiments, the second frame 113 may have a first substrate 175 and a third bracket 173 provided on the first substrate 175, the deployable components 130 are pivotally connected to the third bracket 173, an optical component 120 is provided between the two deployable components 130 and provided on the third bracket 173, and the first rotating portion 114 is provided between the third bracket 173 and the first substrate 175. The above compact structure is conducive to reducing the space occupied by the product, and the design is reasonable.

In some embodiments, as shown in FIG. 10, a torsion component 160 may be provided at the pivot connection between the deployable components 130 and the support component 110, which makes the distal ends of the opposite deployable components 130 depart with respect to each other, so that the proximal ends of the deployable components 130 can maintain a tight abutting relationship with the outer peripheral surface of the first rotating portion 114 under the action of the torsion component 160.

In some embodiments, as shown in FIGS. 10 and 11, the first rotating portion 114 has an arc-shaped peripheral surface, and the arc-shaped peripheral surface is constructed to cause the proximal ends of the deployable components 130, which abut against the arc-shaped peripheral surface, to approach or depart from each other when the first rotating portion 114 rotates.

Specifically, the shape of the arc-shaped peripheral surface can be elliptical, and a smooth layer can be provided outside the arc-shaped peripheral surface to facilitate the sliding of the deployable component 130 along the arc-shaped peripheral surface.

In some embodiments, as shown in FIGS. 10 and 11, the second frame 113 is provided with a limiting portion 115 protruding therefrom, and the first rotating portion 114 has a limiting groove 116 adaptive to the limiting portion 115, so that with the limiting portion 115 mounted in the limiting groove 116, the distal ends of the deployable components 130 maintain a gathered state.

Specifically, the above-mentioned limiting portion 115 can be a convex column, and the limiting groove 116 can be an arc-shaped groove adaptive to the convex column. The two arc-shaped grooves are located on two opposite sides with a spacing of the first length, and the convex columns can be integrally formed on the second frame 113. The structural design of the above-mentioned limiting groove 116 and limiting portion 115 can keep the first rotating portion 114 in the position where the deployable components 130 are in a gathered state, and the first rotating portion 114 will not rotate until it is subjected to external force.

In some embodiments, an arc-shaped convex portion 131 is provided on each deployable component 130 on its proximal inner side, to fit snugly with the circumferential outer wall of the first rotating portion 114. The structural design of the arc-shaped convex portion 131 mentioned above can reduce the contact friction between the deployable components 130 and the first rotating portion 114, facilitating the transformation of the deployable component 130 between the deployed state and the gathered state.

Embodiment 4

Figure 12:
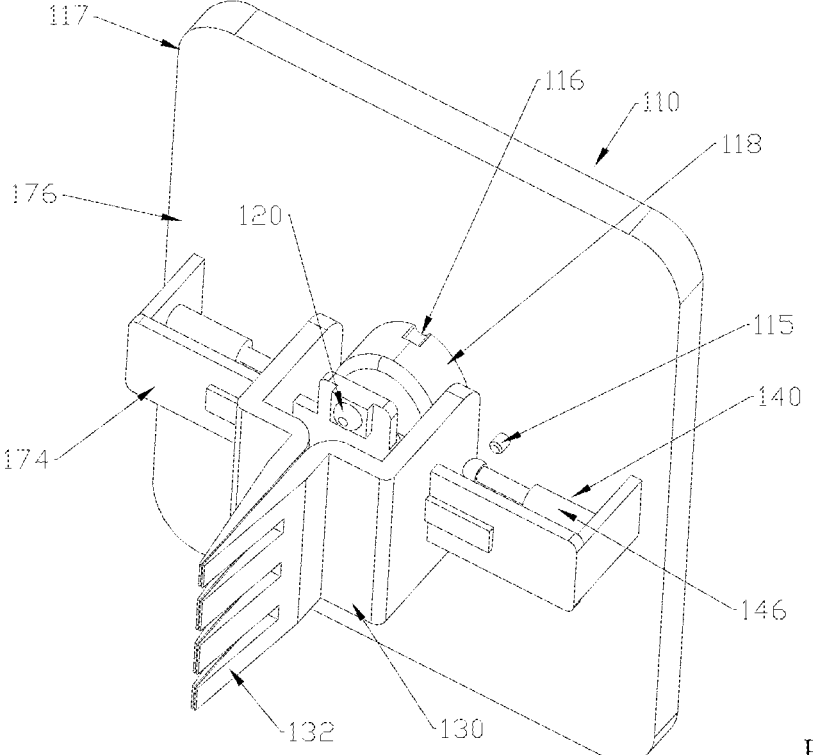
FIG. 12 is a seventh structural schematic diagram of the head optical application device according to the embodiment of the present disclosure, in which the deployable components are in a gathered state.
Figure 13:
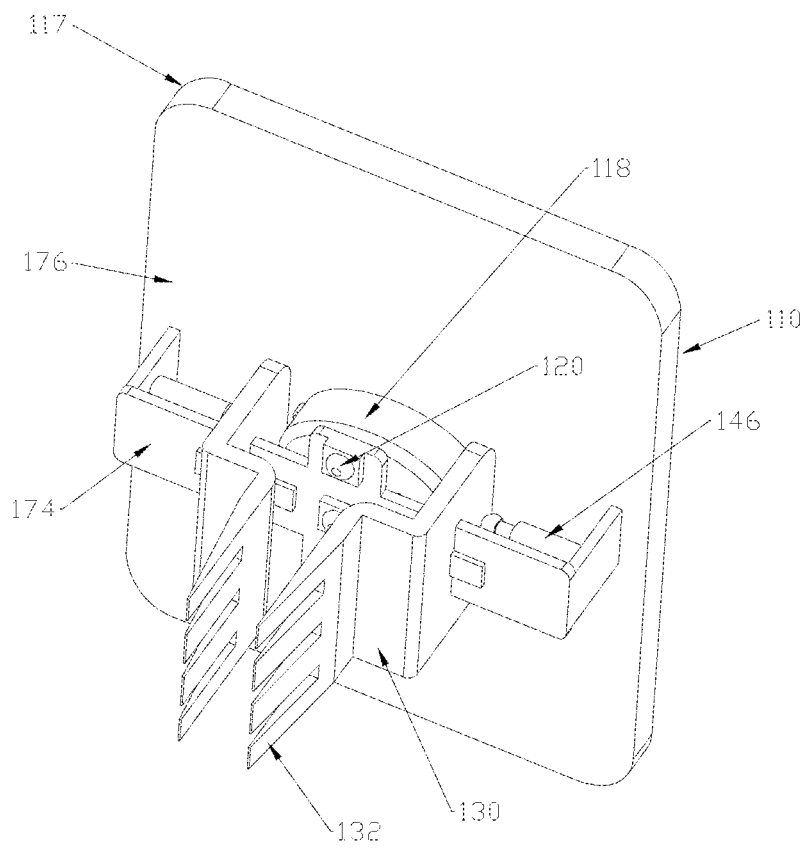
FIG. 13 is a seventh structural schematic diagram of the head optical application device according to the embodiment of the present disclosure, in which the deployable components are in a deployed state.

In some embodiments, as shown in FIGS. 12 and 13, there are at least two deployable components 130, and the support component 110 includes a third frame 117 and a second rotating portion 118 rotatably arranged on the third frame 117. The deployable components 130 are provided on opposite sides of the optical component 120, and the deployable components 130 are slidably provided on the third frame 117. The surface of each deployable component 130 on the proximal inner side abuts against the circumferential outer wall of the second rotating portion 118, the second rotating portion 118 is constructed to push, by means of rotation, the distal ends of the deployable components 130 located on two opposite sides of the optical component 120 to deploy or gather with respect to each other.

Specifically, the second rotating portion 118 may have two opposite sides spaced at a third length, and other two opposite sides spaced at a fourth length, wherein the third length is greater than the fourth length. When the two sides spaced at a third length respectively abut against the proximal sides of the opposite deployable components 130, the deployable components 130 are in a gathered state (as shown in FIG. 12). When the operator rotates the second rotating portion 118 to make the two sides spaced at a fourth length respectively abut against the deployable components 130, the deployable components 130 gradually transform from the gathered state to the deployed state (as shown in FIG. 13).

Specifically, the cross-sectional shape of the second rotating portion 118 mentioned above can be elliptical, irregularly arc-shaped, rectangular, or other shapes, and the present disclosure does not specifically limit this. Preferably, as shown in FIG. 13, the cross-sectional shape of the above second rotating portion 118 is elliptical, which causes the deployable components 130 to gradually deploy from a gathered state, improving the user's use experience.

In some embodiments, as shown in FIGS. 12 and 13, the third frame 117 as mentioned above may have a second substrate 176 and a fourth bracket 174 located on the second substrate 176, a deployable component 130 is slidably provided on the fourth bracket 174, an optical component 120 is located between the two deployable components 130 and on the fourth bracket 174, and a second rotating portion 118 is located between the fourth bracket 174 and the second substrate 176. The above compact structure is conducive to reducing the space occupied by the product, and the design is reasonable.

In some embodiments, as shown in FIGS. 12 and 13, the transmission mechanism 140 includes two telescopic rods 146 arranged on the third frame 117, the inner opposite ends of the two telescopic rods 146 respectively abut against the sides departing from each other of the deployable component 130 located on both sides.

Specifically, the direction of expansion and contraction of the two telescopic rods 146 mentioned above is the same as the sliding direction of the deployable component 130, and the two telescopic rods 146 are respectively located on sides departing from each other of the two deployable components 130. The above telescopic rods 146 are used to apply a force to the deployable components 130 to transform them into a gathered state, so as to push the two deployable components 130 towards each other, so that the proximal inner sides of the deployable components 130 abut tightly against the outer wall of the second rotating portion 118.

Specifically, the aforementioned telescopic rods 146 are provided in one-to-one correspondence with the deployable components 130, so that each telescopic rod 146 can act stably on the corresponding deployable component 130.

In some embodiments, as shown in FIGS. 12 and 13, an insertion portion 132 is formed on the distal side of the deployable component 130, and the insertion portions 132 of the deployable components 130 oppositely provided on the two sides of the optical component 120 can closely fit with each other.

Specifically, as shown in FIG. 12, the insertion portions 132 of the two oppositely provided deployable components 130 can tightly fit when the deployable components 130 are in a gathered state, and the two form a sharp end upon gathering, facilitating the deployment components to insert into the hair in a gathered state.

In some embodiments, the deployable component 130 is pivotally connected to the support component 110, and a torsion component 160 is provided at the pivot connection the two, which makes the distal ends of the opposite deployable components 130 close or depart with respect to each other.

Specifically, as shown in FIGS. 7 and 8, in Embodiment 2, the aforementioned torsion component 160 is used to make the distal ends of the opposite deployable components 130 gather with respect to each other. As shown in FIGS. 10 and 11, in Embodiment 3, the above-mentioned torsion component 160 is used to make the distal ends of the opposite deployable components 130 depart with respect to each other. The force exerted by the aforementioned torsion component 160 on the deployable component 130 can be set according to the specific structure of each embodiment.

In some embodiments, the optical components 120 are plural, a plurality of optical components 120 are provided sequentially along a fifth length direction, and the plurality of deployable components 130 are provided in pairs on the two opposite sides of the optical components 120 along the fifth length direction. And the above plurality of optical components 120 can be arranged along a first width direction perpendicular to the fifth length direction.

Specifically, as shown in FIGS. 1 and 2, the support component 110 is rectangular plate shape and has a fifth length direction. A plurality of optical components 120 are provided sequentially along the fifth length direction, and a plurality of deployable components 130 can be provided in pair on two opposite sides of the optical component 120 along the fifth length direction. The present disclosure does not specifically limit the number of deployable components 130, the number of optical components 120, and the setting method. They are designed based on the application scenario of the head optical application device 100, as long as better effect of emission or reception of light, as well as the hair pushing-aside effect can be achieved. In addition, the above support component 110 can have an arc surface that is adaptive to the arc of the user's head, so as to facilitate the optical component 120 mounted on it to further lean towards the scalp.

In some embodiments, the deployable component 130 has a deployment body 134 and an arc-shaped portion 135 provided on the distal side of the deployment body 134.

Specifically, the arc-shaped portion 135 is located at the tail end, which does not cause discomfort to the user when in contact with the user's scalp or when the deployable component 130 is deployed. The arc-shaped fitting surface of the arc-shaped portion 135 can further improve comfort.

In some embodiments, the arc-shaped portion 135 is made of flexible material, and the flexibility of the material of the arc-shaped portion 135 is greater than that of the material of the deployment body 134. The arc-shaped portion 135 is made of flexible material, so that when it comes into contact with the user's scalp and when the deployable component 130 is deployed, it will not cause excessive pressure on the user's scalp and generate a sense of tenderness.

In some embodiments, the deployment body 134 mentioned above can be made entirely of flexible material or hard material, or can be formed by mixing flexible and hard material, as long as its flexibility is smaller than that of the first arc-shaped portion 135, which allows the deployable component 130 to deploy smoothly under the action of force caused by the surrounding environment, avoiding bending of the deployment body 134 that affects the hair pushing-aside effect. Specifically, the flexibility of the portion of the above deployment body 134 close to the user's scalp may be greater than that of the portion departing from the user's scalp, in order to ensure the comfort of the user when the deployment body 134 is in contact with the user's scalp, meanwhile further ensure the smooth deployment (opening) of the deployment bodies 134 with respect to each other during the deployment process without affecting the hair pushing-aside effect.

In some embodiments, the cross-sectional area of the deployable component 130 gradually decreases from its proximal side to its distal side, allowing the distal end of the deployable component 130 to smoothly insert into the hair gap and abut against the user's scalp.

Specifically, the above deployable component 130 can be in the form of a comb, rectangular plate, triangular plate, or other shapes, so that the cross-sectional area of the deployable component 130 on the proximal side gradually decreases towards its cross-sectional area on the distal side, so as to achieve stable pivot connection between the deployable component 130 and the support component 110 and facilitate the insertion of the distal end of the deployable component 130 into the user's hair gap.

In some embodiments, the deployable component 130 is made of transparent material that can allow passing of light, so as to prevent blocking the light emitted or received by the optical component 120.

In some embodiments, as shown in FIGS. 1 and 2, the distal end of the deployable component 130 contracts inward to form a stepped portion 138.

Specifically, combining FIGS. 1 and 2, the above stepped portion 138 is located on two opposite sides of the arc-shaped portion 135. When the apparatus mounted with the head optical application device 100 is worn, the arc-shaped portion 135 abuts against the user's scalp, and there is a gap between the distal side of the stepped portion 138 and the user's scalp for accommodating hair, so as to compress the hair that has been pushed aside and parted during the deployment process of the deployable components 130, achieving better hair pushing-aside effect.

It should be noted that the distal end of the deployable component 130 in each embodiment of the present disclosure may contract inward to form a stepped portion 138, which is not limited to be applied to the technical solution of embodiment 1. The stepped portion 138 shown in FIGS. 1 and 2 is only an example.

In the following text of the present disclosure, various structural forms of transcranial light regulation apparatus 200 are proposed. It should be noted that a plurality of optical components 120 included by the transcranial light regulation apparatus 200 referred hereinafter can be provided in corresponding positions to various regions of the brain, such as the left and right temporal regions, the top regions, the left and right occipital regions, etc. And all the optical components 120 can emit transcranial light, which is light that can penetrate the skull. The present disclosure will not elaborate further on this matter.

Figure 14:
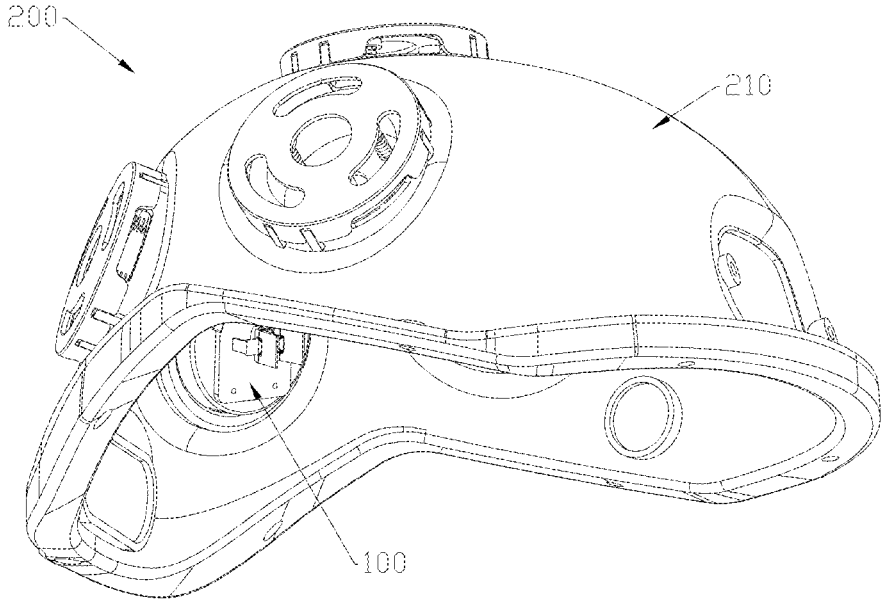
FIG. 14 is a first structural schematic diagram of the transcranial light regulation apparatus according to the embodiment of the present disclosure.

According to some embodiments of the present disclosure, a transcranial light regulation apparatus 200 is further provided. As shown in FIG. 14, the transcranial light regulation apparatus 200 comprises a plurality of head optical application devices 100 mentioned above, as well as a housing 210 for mounting the plurality of head optical application devices 100.

In some embodiments, a plurality of elastic components (not shown in the figures) may be provided between the aforementioned housing 210 and the head optical application device 100, such as springs, and/or an elastic layer, such as a soft rubber layer (such as silicone rubber layer), may be provided on the head optical application device 100 on the side close to the user's scalp, so that when the user wears the transcranial light regulation apparatus 200, the head optical application device 100 can adapt to different user's head shapes under the action of the elastic component and/or elastic layer.

The transcranial light regulation apparatus 200 using the above-mentioned head optical application device 100 can achieve the following mechanism: the distal ends of the deployable components 130 can be inserted into the user's hair gap in a gathered state, and after insertion, the distal ends of the deployable components 130 can push aside and thus part the hair blocking the light in a deployed state, solving the problem of low light propagation rate caused by hair blocking, and achieving optimal usage effect of the transcranial light regulation apparatus 200.

In some embodiments, the housing 210 is mounted with a movable component that can move towards the distal side, and the head optical application device 100 is correspondingly mounted on the movable component to make the head optical application device 100 adhere to the scalp.

Specifically, the above movable component can move towards the direction close to the scalp under the action of the operator's push force, and after moving till the distance to the scalp reaches a preset distance, the head optical application device 100 mounted on the movable component can further approach the scalp. Through the squeeze between the movable component and the scalp, the distal ends of the deployable components 130 of the head optical application device 100 depart from each other to transform into a deployed state, and thus may push aside and part the blocked hair.

Figure 15:
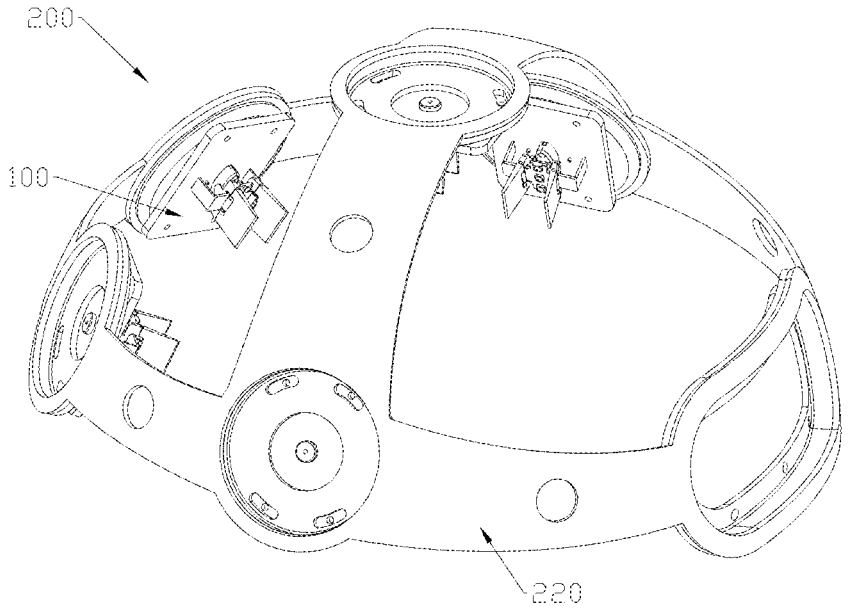
FIG. 15 is a second structural schematic diagram of the transcranial light regulation apparatus according to the embodiment of the present disclosure.

According to some embodiments of the present disclosure, a transcranial light regulation apparatus 200 is further provided. As shown in FIG. 15, the transcranial light regulation apparatus 200 includes a plurality of aforementioned head optical application devices 100, as well as an elastic cross-linked mesh 220 for mounting a plurality of head optical application devices 100.

The design of the elastic cross-linked mesh 220 mentioned above enables it to adapt to different users' head shapes when the users wear it. The elasticity of the elastic cross-linked mesh 220 enables the head optical application device 100 to abut tightly against the scalp. Even facing various head shapes, the tension applied by any portion thereof at the corresponding position on the elastic cross-linked mesh 220 can be transmitted and extended to other positions of the elastic cross-linked mesh 220 using the cross-linking topology structure of the elastic cross-linked mesh 220. This enables the elastic cross-linked mesh 220 to adhere tightly to scalp of any head shape, thereby facilitating the subsequent deployment of the deployable component 130 to push aside and part hair. And the above-mentioned head optical application device 100 can have a certain degree of freedom when assembled on the elastic cross-linked mesh 220, so as to make adaptive adjustments according to the user's head shape, while maintaining a tight fitting relationship between head optical application device 100 and the scalp.

In some embodiments, the above elastic cross-linked mesh 220 may include a plurality of cross connected elastic bands, which form a holding cavity around the user's head. For example, combining with FIG. 15, the elastic cross-linked mesh 220 mentioned above can include a ring body and a band body connecting the two opposite sides of the ring body, the band body is provided corresponding to the top of the user's head, and the ring body is provided around the user's head. The above band body and the ring body can be provided with a plurality of head optical application devices 100. The above is only an example of the specific structure of the elastic cross-linked mesh 220, and the present disclosure is not limited to this.

By way of example, the elastic cross-linked mesh 220 mentioned above can be formed in one piece or by connecting a plurality of elastic bands, and the present disclosure does not specifically limit this.

Figure 16:
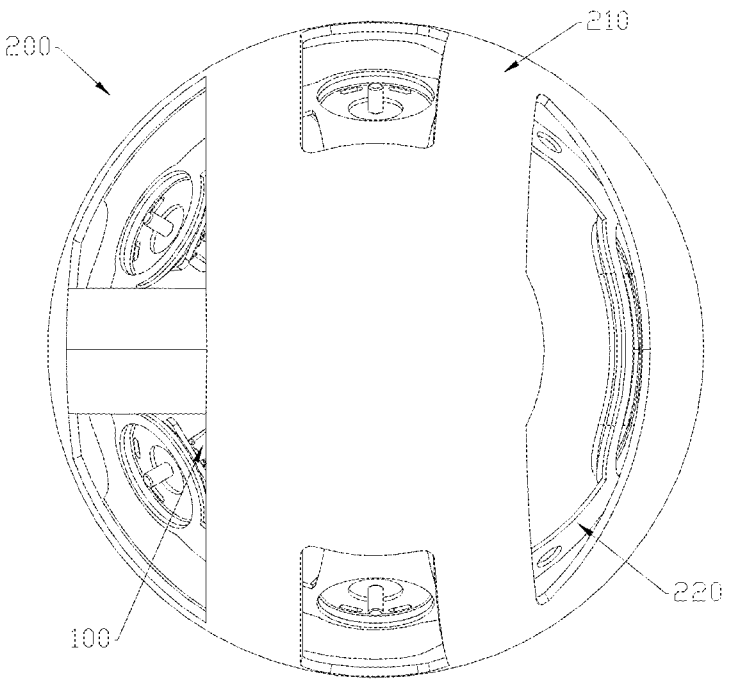
FIG. 16 is a third structural schematic diagram of the transcranial light regulation apparatus according to the embodiment of the present disclosure.
Figure 17:
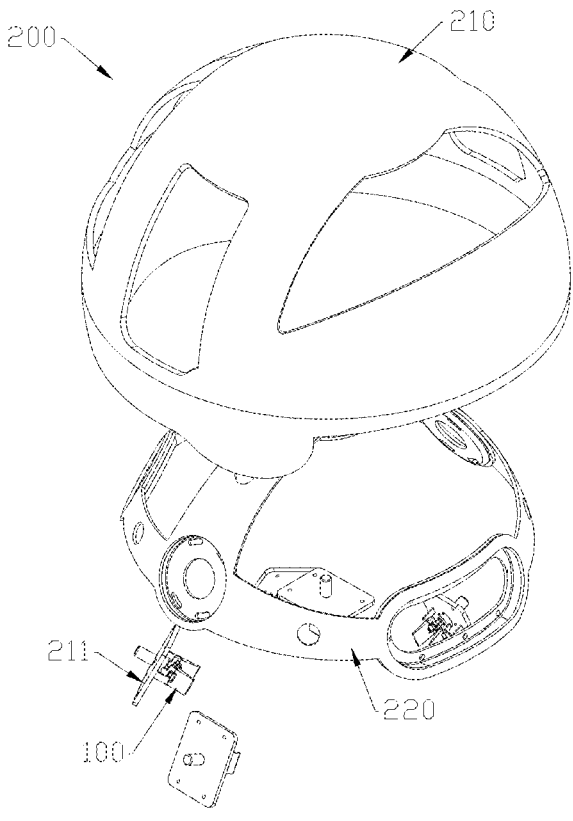
FIG. 17 is an exploded view of the third structure of the transcranial light regulation apparatus according to the embodiment of the present disclosure.

According to some embodiments of the present disclosure, a transcranial light regulation apparatus 200 is further provided. As shown in FIGS. 16 and 17, the transcranial light regulation apparatus 200 includes a plurality of head optical application devices 100 mentioned above, as well as an elastic cross-linked mesh 220 and a housing 210 for mounting the elastic cross-linked mesh 220. A plurality of head optical application devices 100 are arranged on the elastic cross-linked mesh 220.

The above-mentioned housing 210 can be made of harder material to maintain a certain shape, making it convenient for users to wear the above-mentioned transcranial light regulation apparatus 200. At the same time, a plurality of head optical application devices 100 are arranged on the elastic cross-linked mesh 220, enabling the head optical application device 100 to abut tightly against the scalp under the action of the elastic cross-linked mesh 220, which facilitates the subsequent deployment of the deployable component 130 to push aside and part hair and improve the light irradiation rate of the target area on the scalp. Moreover, when worn by users, the elastic cross-linked mesh 220 can adapt to head shapes of different users. Through the above structure, the transcranial light regulation apparatus 200 has the advantages of convenient wearing, good illumination effect, and being able to adapt to head shapes of different users.

In some embodiments, the housing 210 is mounted with a plurality of installation components (not shown in the figures) for mounting the elastic cross-linked mesh 220. Each installation component has a flange at the tail end in the first direction towards the scalp, and has an annular concave portion with a predetermined length on the second direction side of the flange departing from the scalp, thereby enabling the elastic cross-linked mesh 220 to be sleeved on the annular concave portion in a circumferential direction and providing expansion allowance for the sleeved elastic cross-linked mesh 220.

In some embodiments, the above elastic cross-linked mesh 220 may include a plurality of lamellar elastic bands, which are sleeved onto the installation component and embedded in the annular concave portion. The thickness direction of the elastic cross-linked mesh 220 can be understood as facing the direction of the scalp. Through the gap fit between the annular concave portion and the elastic cross-linked mesh 220, the elastic cross-linked mesh 220 can provide more expansion margin when adapting to the head shape of the user meanwhile expanding, and add deformation space for elastic cross-linked mesh 220.

According to some embodiments of the present disclosure, a near-infrared apparatus (not shown in the figures) is further provided, wherein each head optical application device 100 can be mounted on any support component such as a bracket, headgear, etc. that can be worn on the user's head. The near-infrared apparatus using the aforementioned head optical application device 100 can make the distal ends of deployable components 130 to be inserted into the user's hair gap in a gathered state, and the distal ends of the deployable components 130 can push aside and part the hair that blocks light in a deployed state after insertion, solving the problem of low light propagation rate caused by hair blocking, and enabling the near-infrared apparatus to have better measurement results.

Figure 18:
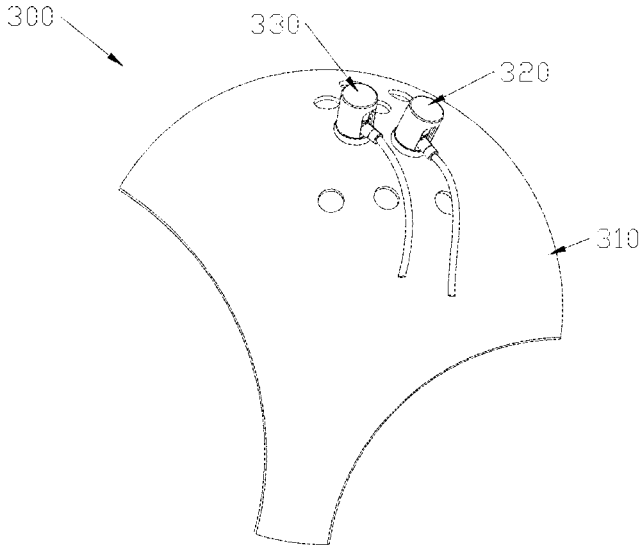
FIG. 18 is a structural schematic diagram of the headgear of a near-infrared apparatus according to the embodiment of the present disclosure.

In some embodiments, as shown in FIG. 18, the near-infrared apparatus further includes a headgear 300 for mounting a plurality of head optical application devices 100. The headgear 300 includes a headgear body 310 for mounting a plurality of head optical application devices 100, on which a plurality of head optical application devices 100 are provided. The plurality of head optical application devices 100 can be constructed as an emitting probe 320 and a receiving probe 330, respectively. The optical components 120 contained in the emitting probe 320 are each light transmission components that emit light, and the optical components 120 contained in the receiving probe 330 are each light receiving components that receive light.

In some embodiments, the above-mentioned light transmission component can be any optical component such as an LED lamp, optical fiber, laser, etc., which can be used to emit near-infrared light to the user's scalp. The above light receiving component can be an optical fiber for receiving light emitted from the user's scalp.

Furthermore, although exemplary embodiments have been described herein, their scope includes any and all embodiments having equivalent elements, modifications, omissions, combinations (e.g., schemes crossed by various embodiments), adaptations or changes based on the present disclosure. The elements in the claims will be interpreted broadly based on the language used in the claims, not limited to the examples described in the description or during the implementation of the present application, and the examples will be interpreted as non-exclusive. Therefore, the specification and examples are intended to be considered as examples only, and the true scope and spirit are indicated by the following claims and the full scope of their equivalents.

The above description is intended to be illustrative rather than restrictive. For example, the above examples (or one or more of them) may be used in combination with each other. For example, those skilled in the art may use other embodiments when reading the above description. In addition, in the above specific embodiment, various features can be grouped together to simplify the present disclosure. This should not be interpreted as the intention that a public feature that does not require protection is necessary for any claim. On the contrary, the subject matter of the present application may be less than all the features of a particular disclosed embodiment. Thus, the following claims are hereby incorporated into the specific embodiments as examples or embodiments, wherein each claim is independently regarded as a separate embodiment, and it is considered that these embodiments can be combined with each other in various combinations or arrangements. The scope of the present application shall be determined by reference to the full scope of the appended claims and the equivalent forms empowered by these claims.

The above embodiments are only exemplary embodiments of the present disclosure and are not intended to limit the present disclosure. The protection scope of the application is defined by the claims. Those skilled in the art may make various modifications or equivalent substitutions to the present disclosure within the substance and protection scope of the present disclosure, and such modifications or equivalent substitutions shall also be deemed to fall within the protection scope of the application.

What is claimed is:

1. A head optical application device, wherein, the head optical application device comprises:

a support component, which is constructed to mount an optical component;

the optical component, which is constructed to transmit light to or receive light from scalp;

at least two deployable components, which are provided on the support component, and are constructed to deploy or gather the distal ends under the action of force caused by the surrounding environment;

wherein the support component comprises a second frame and a first rotating portion rotatably provided on the second frame, each of the deployable components is pivotally connected to the second frame and distributed on two opposite sides of the optical component, the surface of each deployable component on the proximal inner side abuts against the circumferential outer wall of the first rotating portion, the first rotating portion is constructed to drive, by means of rotation, the proximal ends of the deployable components located on two opposite sides of the optical component to deploy or gather with respect to each other.

2. The head optical application device according to claim 1, wherein, the deployable components are constructed to deploy or gather the distal ends of the deployable components under the action of manual force in the surrounding environment.

3. The head optical application device according to claim 2, wherein the support component is further constructed to be movable along the first direction towards the distal side under the manual force, or be able to rise and fall along the second direction of hair growth under the action of the manual force.

4. The head optical application device according to claim 1, wherein, the first rotating portion has two opposite sides spaced at a first length, and other two opposite sides spaced at a second length, wherein the first length is greater than the second length.

5. The head optical application device according to claim 1, wherein, the first rotating portion has an arc-shaped peripheral surface, and the arc-shaped peripheral surface is constructed to cause the proximal ends of the deployable components, which abut against the arc-shaped peripheral surface, to approach or depart from each other when the first rotating portion rotates.

6. The head optical application device according to claim 1, wherein, the second frame is provided with a limiting portion protruding therefrom, and the first rotating portion has a limiting groove adaptive to the limiting portion, so that with the limiting portion mounted in the limiting groove, the distal ends of the deployable components remain a gathered state.

7. The head optical application device according to claim 1, wherein, an arc-shaped convex portion is provided on each deployable component on its proximal inner side, to fit snugly with the circumferential outer wall of the first rotating portion.

8. The head optical application device according to claim 1, wherein, the deployable components are made of a second deformable material, and the support component is further constructed to transform the distal ends of the deployable components from gathering with respect to each other into deploying with respect to each other through deformation when moving along the first direction towards the distal side under the action of manual force.

9. The head optical application device according to claim 8, wherein, each deployable component includes a first body provided on the support component and a second body provided on the distal side of the first body, the proximal end of the second body of each deployable component lean against each other and gradually deploys towards its distal end.

10. The head optical application device according to claim 1, wherein, a sliding guide surface is provided on the distal end of the deployable component, and the sliding guide surface is constructed so that the force applied to the distal end of the deployable component for deploying is greater than the force applied to the distal end of the deployable component for gathering.

11. The head optical application device according to claim 1, wherein, the deployable components are pivotally connected to the support component, and a torsion component is provided at the pivot connection of the two, which makes the distal ends of the opposite deployable components close or depart with respect to each other.

12. The head optical application device according to claim 1, wherein, the optical components are plural, the plurality of optical components are sequentially provided along a fifth length direction, and the plurality of deployable components are provided in pairs on the opposite sides of the optical components along the fifth length direction.

13. The head optical application device according to claim 12, wherein, the plurality of optical components are arranged along a first width direction perpendicular to the fifth length direction.

14. The head optical application device according to claim 1, wherein the deployable component has a deployment body and an arc-shaped portion located on the distal side of the deployment body.

15. The head optical application device according to claim 14, wherein, the arc-shaped portion is made of flexible material, and the flexibility of the material of the arc-shaped portion is greater than that of the material of the deployment body.

16. The head optical application device according to claim 1, wherein the cross-sectional area of the deployable component gradually decreases from its near side to its distal side.

17. The head optical application device according to claim 1, wherein the deployable component is made of transparent material that can transmit light.

18. The head optical application device according to claim 1, wherein the distal end of the deployable component contracts inward to form a stepped portion.

19. A transcranial light regulation apparatus, which comprises a plurality of head optical application devices of claim 1, and a housing for mounting the plurality of head optical application devices.

20. A near-infrared apparatus, which comprises a plurality of head optical application devices of claim 1, as well as a headgear for mounting the plurality of head optical application devices, each optical component is a light transmission component or a light reception component, and the headgear is provided with a plurality of light transmission components and a plurality of light reception components thereon.

* * * * *